(12) United States Patent
Yoneda et al.

(10) Patent No.: US 7,794,950 B2
(45) Date of Patent: Sep. 14, 2010

(54) METHOD FOR THE DETECTION OF IRRADIATION TREATMENT OF FOODS

(75) Inventors: Yukio Yoneda, Osaka (JP); Toshihiro Yamada, Osaka (JP)

(73) Assignee: Nissin Food Products Co., Ltd., Osaka-shi (JP)

( * ) Notice: Subject to any disclaimer, the term of this patent is extended or adjusted under 35 U.S.C. 154(b) by 968 days.

(21) Appl. No.: 11/145,191

(22) Filed: Jun. 6, 2005

(65) Prior Publication Data

US 2006/0057655 A1 Mar. 16, 2006

(30) Foreign Application Priority Data

Jun. 7, 2004 (JP) .............................. 2004-169185

(51) Int. Cl.
*G01N 33/53* (2006.01)

(52) U.S. Cl. ...................................... 435/7.1; 436/548

(58) Field of Classification Search .................. 435/7.1, 435/7.2, 7.91, 7.92
See application file for complete search history.

(56) References Cited

U.S. PATENT DOCUMENTS 4,985,270 A * 1/1991 Singer et al. ................. 426/565
5,698,281 A * 12/1997 Bellantoni et al. .......... 428/35.7

FOREIGN PATENT DOCUMENTS

JP 2003-102435 * 4/2003
WO WO 9613174 * 5/1996

OTHER PUBLICATIONS

English Translation of JP2003-102435 (by Mizuno et al.).*
Katial et al; "Deleterious effects of electron beam radiation on allergen extracts;" J Allergy Clin Immunol. (Aug. 2002); pp. 215-219. (see specification).
Lee et al; "Effects of Gamma Radiation on the Allegenic and Antigenic Properties of Milk Proteins;" J Food Protection; vol. 64, No. 2 (2001); pp. 272-276. (see specification).
Byun et al; "Effects of gamma Radiation on the Conformational and Antigenic Properties of a Heat-Stable Major Allergen in Brown Shrimp;" J Food Protection, vol. 63, No. 7 (2000) pp. 940-944. (see specification).
Yang et al; "Changes in Biochemical Properties of Ovomucoid by Radiation;" Radial. Phys. Chem. vol. 48, No. 6 (1996) pp. 731-735. (see specification).
Kume et al; "Immunochemical Identification of Irradiated Chicken Eggs;" J Sci Food Agric, 65 (1994) pp. 1-4. (see specification).

* cited by examiner

*Primary Examiner*—Jacob Cheu
(74) *Attorney, Agent, or Firm*—Kratz, Quintos & Hanson, LLP

(57) ABSTRACT

An object of the present invention is to provide a novel method for detecting irradiation treatment of foods. The present invention provides a method for detecting irradiation treatment of foods comprising the steps of (A) obtaining a fraction containing one or more irradiation-generated fragments of natural high-molecular weight compound(s) from a food sample, and (B) reacting the fraction with one or more antibodies capable of recognizing the one or more fragments, thereby detecting the one or more fragments. The invention also provides a kit for detecting irradiation treatment of foods.

11 Claims, 4 Drawing Sheets

METHOD FOR THE DETECTION OF IRRADIATION TREATMENT OF FOODS

BACKGROUND OF THE INVENTION (1) Field of the Invention

The present invention principally relates to a method for the detection of irradiation treatment of foods and a kit therefor.

(2) Description of the Related Art

Conventionally, food products have been processed by ionizing radiation in order to inhibit germination; slow down the ripening; sterilize; kill insect pests; improve the restoration ability of dehydrated vegetables, the extraction efficiency of an active ingredient, flavor; etc. The irradiation treatment has advantages in that it is applicable to packaged end-products or frozen foods; mass treatment is possible; loss of flavor, taste, and nutrients can be reduced; and the treatment does not induce radioactivity in food because the radiation energy is finally converted into heat energy.

Radiation sources approved for food irradiation are γ rays of [$^{60}$Co] or [$^{137}$Cs], electron beams with 10 MeV or less, and X-rays with 5 MeV or less.

In 1981, with respect to the safety of irradiated foods, the Joint FAO/IAEA/WHO Expert Committee concluded that "food irradiation with a dosage not exceeding 10 kGy will not prejudice the wholesomeness of the foods". Furthermore, in 1997, WHO concluded that foods irradiated with a dosage ranging from 10 kGy to 57 kGy are both safe to consume and nutritionally adequate".

In the EU (European Union), the BCR (Community Bureau of Reference) programme undertook a research project to develop standardised detection methods from 1990 to 1993, and examined detection methods that had been studied up to then. Based on the research and examination results, nine standard reference methods were established in the EU by 2002 (Table 1). Note that these standard methods are adopted as General Codex Methods, which was accepted at the Codex general meetings in 2001 and 2003.

TABLE 1

| Method | EN number | Analysis target |
| --- | --- | --- |
| GC analysis of hydrocarbons | EN 1784 | Irradiated food containing fat |
| GC/MS analysis of 2-alkylcyclobutanones (2-ACBs) | EN 1785 | Irradiated food containing fat |
| Electron Spin Resonance (ESR) spectroscopy | EN 1786 | Irradiated food containing bone |
| Electron Spin Resonance (ESR) spectroscopy | EN 1787 | Irradiated food containing cellulose |
| Thermoluminescence (TL) detection | EN 1788 | Irradiated food from which silicate minerals can be isolated |
| Electron Spin Resonance (ESR) spectroscopy | EN 13708 | Irradiated food containing crystalline sugar |
| Direct Epifluorescent Filter Technique/Aerobic Plate Count (DEFT/APC) | EN 13783 | Irradiated food (screening method) |
| DNA Comet Assay | EN 13784 | Irradiated food (screening method) |
| Photostimulated Luminescence (PSL) | EN 13751 | Irradiated food containing silicate minerals (screening method) |

GC: gas chromatograph, 2-ACBs: 2-alkylcyclobutanones, GC/MS: gas chromatograph/mass spectrometry, ESR: electron spin resonance spectroscopy, TL: Thermoluminescence, DEPT/APC: direct epifluorescent filter technique/aerobic plate count, PSL: photostimulated luminescence In addition to these analytical methods, numerous physical, chemical, and biological detection methods are known, but in most cases they have not been technically established (Table 2).

TABLE 2

| Method (principle) | Evaluation | Analysis target |
| --- | --- | --- |
| *Physical detection methods* | | |
| Electrical impedance measurement method | B | Irradiated potato |
| Viscosity measurement method | C | Irradiated pepper |
| Differential scanning calorimeter (DSC) method | A | Irradiated fish, shrimp, egg white |
| Near-infrared spectroscopy (NIR) | A | Irradiated spices |
| Chemiluminescent method | B | Irradiated frozen chicken,wheat |
|  | A | Irradiated shellfish, crustacean, chicken bone |
| *Chemical detection method* | | |
| o-tyrosine method | B | Irradiated chicken, shrimp, shellfish, fish, frog leg, egg white |
| MS crosslinking analysis of proteins | A | Irradiated fish, shrimp, egg white |
| Low molecularization (Reduced allergenicty) | A | Irradiated shrimp, milk protein |
| Immunoassay of 2-ACBs | B | Irradiated food containing fat |
| Degraded nucleic acid base (Immunoassay) | B | Irradiated wheat shrimp |
| Cleavage of nucleic acid (pulsefield electrophoresis) | B | Irradiated beef liver, meat fish, shrimp |
| *Biological detection methods* | | |
| Inhibition of cell division | B | Irradiated onion, tubers |
| Deletion of re-epithelialization of the wound | B | Irradiated potato |
| Inhibition of germination ability | C | Irradiated citrus |
| (Half embryo test) | B | Irradiated apple, grains, potato, etc |
| chromosomal aberration | A | Irradiated grains |
| Varied flora | B | Irradiated strawberries, fish, shrimp |
| Limulus test (LAL/GNB) | D | Irradiated chicken |

A: Concept is promising.
B: Further interlaboratory trials are desirable.
C: Crosscheck is in a preparation state or completed.
D: Validity has been verified by the results of a laboratory crosscheck. (Setsuko TODOROKI, RADIOISOTOPES, 2000, 49: pp. 467-469, partially modified)
DSC: differential scanning calorimeter, NIR: near infrared, LAL/GNB: Limulus amoebocyte lysate/Gram negative bacterial count.

A method using a pulsed PSL system that was carried out in Britain yielded satisfactory results among the above-mentioned prior methods. However, it later turned out that this method is strongly influenced by the preservation state of the sample, and it may result in signal fade when the foods are stored in an unsuitable manner or heat-treated. Detection methods whose reliability has been established to some extent (hydrocarbon method, 2-ACBs method, etc.) require an expensive measurement device or a skilled engineer, and thus such a method is of low practicality in view of measurement time and cost performance.

As analytical methods using an antigen-antibody reaction, the above-mentioned immunoassay detection methods that detect 2-alkylcyclobutanones (2-ACBs) or damage(s) in nucleic acid bases have been attempted, but the methods have not been accepted as an official analytical method.

As is clear from the above, the conventional detection methods have some drawbacks in that the methods are sensitive to the preservation state of the sample; an expensive device or a skilled engineer is required; it takes a long time; the cost is high; or the methods are not applicable to heat-sterilized foods.

The standards such as the Codex International Food Standards prescribe that irradiated foods are to be labeled on the package so that consumers can easily understand that the food has been treated by irradiation. Thus, consumer judgment as to whether a food has been treated by irradiation depends on the label according to the Standards. In order to popularize the irradiation treatment technique and to enable consumers to make an informed choice with respect to irradiated food, a simple detection method needs to be popularized at food handling sites which can appropriately detect irradiation treatment of foods not depending on the label. Furthermore, even when food has been appropriately irradiated, there are some cases in which such irradiated food is unfairly labeled and imported. Therefore, in addition to the labeling requirements under the Food Standard, it is necessary to actually detect irradiation treatment of foods so as to avoid importing such unfairly labeled irradiated foods.

Therefore, a method has been strongly demanded which simply and quickly detects irradiation treatment of foods while requiring no expensive device and any skilled engineer as is required in the conventional method.

The irradiation treatment is known to have an influence on various natural high-molecular weight compounds, leading to fragmentation and polymerization of the irradiated natural high-molecular weight compounds. In connection with an immunological reaction, several researches on the reduced allergenicity of irradiated allergens have been conducted. (Yang J-S., et al., *Radiat. Phys. Chem.*, 1996, 48: 731-735 (ovomucoid, ovalbumin); Byun M-W., et al., *J. Food Prot.*, 2000, 63: 940-944 (shrimp allergen, HSP); Lee J-W., et al., *J. Food Prot.* 2001, 64:272-276 (milk$\alpha$-casein, $\beta$-lactoglobulin); Katial R K., et al., *J. Allergy Clin. Immunol.* 2002, 110: 215-219 (electron-irradiation sterilization and reduction/disappearance of allergenicity).

Moreover, protein fragmentation due to irradiation has been clarified by Kume, et al., (Kume T., et al., *J. Sci. Food Agric.*, 1994, 65: 1-4).

An object of the invention is to provide a novel method for the detection of irradiation treatment of foods.

BRIEF SUMMARY OF THE INVENTION

The present inventors conducted extensive research to achieve these objects, and noticed that a natural high-molecular weight compound is fragmented by irradiation. Thus, the inventors found that irradiation treatment of foods can be detected by obtaining a fraction that contains one or more irradiation-generated fragments of natural high-molecular weight compound(s) from a food sample, reacting the fraction with one or more antibodies capable of recognizing the one or more fragments, and detecting the one or more fragments. Based on this finding, the inventors have accomplished the invention.

Upon irradiation, a natural high-molecular weight compound contained in food is lowered in molecular weight (fragmentation), or is raised in molecular weight (aggregation). Among these phenomena, the inventors focused on the phenomenon that a natural high-molecular weight compound is lowered in molecular weight. The invention basically includes the following steps of fractionating a food sample; removing a fraction containing a non-fragmented natural high-molecular weight compound and its aggregates raised by irradiation; and collecting a fraction containing one or more fragments that are lowered in molecular weight by irradiation. Subsequently, one or more antibodies capable of recognizing one or more fragments that are lowered in molecular weight by irradiation are made to act on the collected fraction to detect the one or more fragments. Note that the description of this paragraph is intended to facilitate understanding of the principle of the present invention, and the invention is not limited thereto.

More specifically, the present invention provides the following:

Item 1. A method for detecting irradiation treatment of food comprising the steps of (A) obtaining a fraction containing one or more irradiation-generated fragments of natural high-molecular weight compound(s) from a food sample, and (B) reacting the fraction with one or more antibodies capable of recognizing the one or more fragments, thereby detecting the one or more fragments.

Item 2. A method according to Item 1, wherein the fraction of the step (A) is obtained by filtering.

Item 3. A method according to Item 1 or 2, further comprising, prior to the step (A), the step (A$_0$) of pre-filtrating the food sample.

Item 4. A method according to any one of Items 1 to 3, wherein in the step (B), the one or more fragments are detected by at least one method selected from the group consisting of ELISA (enzyme-linked immunosorbent assay) and immunochromatography.

Item 5. A method according to any one of Items 1 to 4, wherein the food is at least one member selected from the group consisting of eggs, meat, fish and shellfish, spices (herbs and spices), cereals, potatoes, vegetables, beans/seeds, mushrooms, fruit, seaweed, milk, and processed foods thereof.

Item 6. A method according to Item 5, wherein the food is at least one member selected from the group consisting of chicken eggs, beef, pork, shrimp, wheat, soybeans, black pepper, white pepper, sesame, nutmeg, cabbage, welsh onion, and processed foods thereof.

Item 7. A method according to any one of Items 1 to 6, wherein the natural high-molecular weight compound is a protein.

Item 8. A method according to anyone of Items 1 to 7, wherein a molecular weight of the one or more fragments is 30000 or less.

Item 9. A method according to any one of Items 1 to 8, wherein the one or more antibodies are monoclonal or polyclonal antibodies that specifically recognize one or more fragments generated by irradiation.

Item 10. A kit for detecting irradiation of food comprising: a fractionator for obtaining a fraction containing one or more irradiation-generated fragments of natural high-molecular weight compound(s) from a food sample, and one or more antibodies capable recognizing the one or more fragments.

Hereinafter, the present invention is described in more detail.

In this specification, the invention is described with respect to a specific food cited as an example, but the invention is not limited thereto. The invention is applicable to any other food in the same manner.

There is no limitation to the "Food" of the invention, insofar as animals including humans can eat or drink it. Specific examples are as follows:

eggs (such as a chicken egg, quail egg, duck egg, and ostrich egg), meat (such as beef, pork, chicken, mutton, lamb, goat, rabbit, horse, whale, deer, wild boar, frog, soft-shelled turtle, locust, bee, wild duck, quail, domestic duck, pheasant, turkey, sparrow, and ostrich), fish and shellfish (such as shrimp, cuttlefish, octopus, crab, ark shell, short-necked clam, abalone, oyster, top shell, freshwater clam, hard clam, scallop, blue mussel, pacific gaper, horse mackerel, conger, sweetfish, frogfish, chicken grunt, sardine, eel, oceanic bonito, flounder, filefish, silver whiting, carp, salmon, mackerel, shark, Spanish mackerel, Pacific saury, shishamo smelt, seaperch, sea bream, codfish, loach, herring, sea eel, globefish, crucian carp, yellowtail, tuna, pond smelt, jellyfish, squilla, sea cucumber, sea squirt, sea urchin, salmon caviar, herring roe, and caviar), spices (such as hempseed, turmeric, chamomile, mustard, gardenia, watercress, clove, poppy seed, black pepper, white pepper, sesame, coriander, saffron, prickly ash, beefsteak plant, cinnamon, ginger, spare mint, sage, time, turmeric, red pepper, nutmeg, garlic, bay leaf, basil, vanilla, parsley, Japanese mint, paprika, peppermint, yuzu (Citrus junos), mugwort, rosemary, rose hip, wasabi (Japanese horseradish), and tea leaves), cereals (such as Amaranthus, foxtail millet, oat, barley, dogtooth violet, wild oat, millet, wheat, rice, buckwheat, corn, adlay, sawa millet, and rye), potatoes (such as sweet potato, taro, potato, and yam), vegetables (such as artichoke, chive, Angelica Keiskei, asparagus, alfalfa, udo, okra, turnip, pumpkin, cauliflower, dried gourd strips, chrysanthemum, cabbage, canola, cucumber, arrowhead, kale, burdock root, Komatsuna, szechwan pickle, sweet pepper, Japanese parsley, celery, flowering fern, Japanese radish, leaf mustard, bamboo shoot, onion, Qing gin cai, reproductive shoot of field horsetail, wax gourd, tomato, eggplant, shepherd's purse, karela, leek, carrot, white welsh onion, scallion, Chinese cabbage, radish, beat, bell pepper, butterbur, broccoli, spinach, mitsuba (Japanese trefoil leaf), myoga (Japanese ginger), mulukhiya, lily bulb, shallot, lettuce, lotus root, and bracken), beans/seeds (such as almond, azuki bean, kidney bean, green peas, cacao, cashew nut, ginkgo nut, chestnut, walnut, poppy, coconut, coffee bean, winged bean, broad bean, soybean, date, pistachio, sunflower seed, chickpea, hazelnut, macadamia nut, pine seed, peanut, and lentil), mushrooms (such as velvet shank, shiitake mushroom, hon-shimeji (*Lyophyllum aggregatum* Kühner), nameko mashroom, hiratake mushroom (*Pleurotus ostreatus*), maitake mushroom, mushroom, and matsutake mushroom), fruits (such as Akebi (akebia quinata), acerola, avocado, apricot, strawberry, fig, iyokan (Citrus iyo), ume (Japanese apricot), Satsuma orange, olive, orange, persimmon, kabosu lime, Chinese quince, kiwi fruit, guava, goumi, grapefruit, cherry, pomegranate, shekwasha, watermelon, sudachi (Citrus sudachi), plum, durian, Japanese summer orange, pineapple, hasukappu, hassaku orange, banana, papaya, loquat, grape, blueberry, shaddock, ponkan orange, mango, melon, peach, litchi, lime, raspberry, apple, and lemon), seaweed (such as, sea lettuce, green laver, spontaneous purple laver, sea tangle, Ceylon moss, hijiki (edible brown algae), mozuku seaweed (*Nemacystus decipiens*), and wakame seaweed, and milk (such as cow's milk, human milk, and goat's milk).

Usable is a processed food prepared from at least one member selected from the above as a starting material or a mixture of two or more members. Any foods other than the above also can be used. In addition, food additives, such as a gelling agent, fall under the category of foods of the invention.

Processed food means any food subjected to processing (giving to food a new characteristic while maintaining the essential characteristics of the food) such as cooking with heat and other ways of cooking, such as freezing, drying, freeze-drying, milling, crushing, separating, salting, seasoning, etc.

Among the above-mentioned foods, the invention is envisaged to be practically applied especially to foods that can be possibly irradiated to prevent germination (inhibiting toxin production and improving the shelf life), control maturity, modify a food component (promote restoration, improvement in ingredient extraction), sterilize, kill insect pests, improve flavor, etc., or foods that can be possibly grown, bred, processed, etc., in a radioactive contaminated area.

Note that food may have a possibility of being irradiated, and does not need to be actually irradiated.

In the invention, as a food sample, the above-mentioned food may be used as it is, or it may be suitably processed.

The food sample is suitably processed depending on the form and properties of the food to be processed. In the case of a liquid-like food, such as an egg or milk, the food may be used as it is or it may be concentrated or diluted with a suitable solvent, for use as a food sample. In the case of a semi-solid or a solid food, such as meat, spices, vegetables, and fruits, the food may be ground using a mixer, a food cutter, a mill, and the like, and then dissolved or suspended in a suitable solvent for use as a food sample. In the case of a powdered food, such as flour, the food is dissolved or suspended in a suitable solvent for use as a food sample. During the above-mentioned process, stirring and mixing, homogenization, dilution, concentration, etc., may be conducted as required. When a target food is a mixture of two or more kinds of food, a food sample may be prepared from the mixture, but it is desirable to separately prepare food samples considering the kind of each food of the mixture. The process of dissolution or suspension in a solvent is not necessarily required.

Examples of a solvent for the preparation of a food sample include water, a Tris buffer (such as a Tris-hydrochloride buffer, a Tris-glycine buffer, or TBS), a phosphate buffer (such as PBS or a citrate-phosphate buffer), Good's buffer (such as MES, MOPS, BES, TES, HEPES, Tricine), a glycine-sodium hydroxide buffer, a carbonate buffer, an acetic acid buffer, a veronal-hydrochloride buffer, a triethanolamine buffer, a boric acid buffer, a glycylglycine-sodium hydroxide buffer, or a solvent using any one of the above as a base. However, the solvent is not limited to the above.

It is desirable that the food sample has a form suitable for fractionation, and it is usually in the form of a liquid or a sol.

A suitable surfactant may be contained in the food sample, as required. By adding a surfactant to the food sample, there are some cases in which solubilization of a membrane protein and a strongly-hydrophobic natural high-molecular weight compound is promoted, and the recovery of the one or more fragments generated by irradiation is improved.

Examples of such surfactants include an anionic surfactant (SDS), a cationic surfactant (CTAB), an ampholytic surfactant (SB-12), a nonionic surfactant (Triton X-100, Tween20, Nonidet P-40, octylglucoside), or bile acids (cholic acid, deoxycholic acid), but not limited thereto.

An SH oxidizing agent and/or reducing agent may be added to the food sample, as required. By adding the SH oxidizing agent and/or reducing agent to the food sample, SH groups in a molecule (in most cases, the larger molecule contains a larger amount of SH groups) is affected by the SH oxidizing agent and/or reducing agent, which may improve the fractionation efficiency of the above-mentioned one or more fragments.

There is no limitation to the SH oxidizing agent and/or reducing agent, and, for example, a mixture of a reduced glutathione (GSH) and an oxidized glutathione (GSSG) (i.e., GSH-GSSG mixture), 2-mercaptoethanol, etc., are preferable (but not limited thereto).

If needed, the food sample may be heat-treated, and then the precipitate may be removed. Thus, by heat-treating the food sample and then removing the precipitate, there are some cases in which the fraction accuracy is increased and the detection sensitivity is improved.

The conditions for heating the food sample are suitably determined according to the kind of one or more fragments of natural high-molecular weight compound(s) to be detected, the kind of components contained in the food sample other than the one or more fragments to be detected, the kind of solvent used for preparing the food sample, the food processing level, etc. For example, when a food sample is an egg sample (50 mM Tris-HCl buffer, pH of 7.6), the detection sensitivity can be improved by a heat treatment, such as boiling for about 10 minutes or incubation at about 80° C. for about 30 minutes.

The heat-treatment is, as required, followed by a routine procedure such as cooling (for example, cooling with running water for about 1 hour) or centrifugation, thereby removing insoluble substances.

Before fractionation, pre-filtering may be conducted, if needed. When both pre-filtering and the aforementioned heat treatment are conducted, pre-filtering is preferably done after the heat treatment. Pre-filtering may reduce, in advance, compounds that have an action of inhibiting the fractionation, thereby increasing the fractionation accuracy, which may improve the detection sensitivity. The kind of prefilter is suitably determined in view of its influence on the detection sensitivity of the one or more fragments to be fractionated, etc.

Preferable examples of such prefilters include Millex-HV (hydrophilic PVDF) (pore size of 0.45 µm, Nihon Millipore K.K.), Millex-GV (hydrophilic PVDF) (pore size of 0.22 µm, Nihon Millipore K.K.). However, other filter membranes can be suitably used when the influence on the detection sensitivity is confirmed. The pre-filtering can be performed according to the operation guide for the prefilter to be used or according to a common procedure.

When a food from which a food sample is prepared as described above has been treated by irradiation, the prepared food sample contains one or more irradiation-generated fragments of the various kinds of natural high-molecular weight compounds that are contained in the food.

In the invention, the natural high-molecular weight compound is at least one member selected from the group consisting of a protein, polysaccharide, and lipid that are contained in the above-mentioned food, and protein is especially preferable.

Examples of the proteins include a simple protein consisting of amino acids and a conjugated protein containing amino acids and components other than amino acids (e.g., glycoprotein, nucleoprotein, lipoprotein, phosphoprotein, chromoprotein, metalloprotein, and a mixture thereof).

Examples of proteins include albumin (such as egg ovalbumin and serum albumin), globulin (such as egg ovoglobulin, β-lactoglobulin of milk, and serum globulin of plasma), actin, myosin, hemoglobin, myoglobin, troponin, tropomyosin (such as Pen a 1 of shrimp), α-actinin, seed storage protein (such as Gly m 1 of soybean, glycinin or β-conglycinin of soybean, legumin or vicilin of broad bean, arachin of peanut, and phaseolin of kidney bean), prolamin (such as gliadin of wheat, hordein of barley, secalin of rye, avenin of oat, zein of corn), glutelin (such as glutenin of wheat, oryzenin of rice), and are not limited thereto.

In this specification, the "one or more irradiation-generated fragments of natural high-molecular weight compound(s)" denotes one or more fragments of a natural high-molecular weight compound that are lowered in molecular weight by irradiation. More specifically, the "one or more irradiation-generated fragments of natural high-molecular weight compound(s)" denotes a part of the natural high-molecular weight compound that was generated by fragmentation of the natural high-molecular weight compound contained in a food by irradiation. Although the invention does not envisage one or more fragments that are generated by factors other than irradiation (for example, enzyme, heat, and mechanical force), one or more fragments generated by factors other than irradiation treatment may be contained in the fraction of the invention insofar as the invention can achieve the desired effect.

There is no limitation to the molecular weight of the one or more irradiation-generated fragments of natural high-molecular weight compound(s) insofar as the molecular weight is lower than that of the compound before irradiation. The molecular weight of the one or more fragments preferably falls within a range such that the one or more fragments can be fractionated from a non-fragmented natural high-molecular weight compound and that the one or more fragments can be recognized by one or more antibodies. The molecular weight of the one or more irradiation-generated fragments of natural high-molecular weight compound(s) is, for example, from 500 to 100000, preferably from 1500 to 70000, and more preferably from 3000 to 30000.

The above-described food sample is fractionated according to the invention, yielding a fraction containing the one or more irradiation-generated fragments of natural high-molecular weight compound(s).

Examples of the fractionation method include filtering, gel chromatography, column chromatography using another carrier (affinity chromatography, ion exchange chromatography, hydrophobic chromatography, reversed phase chromatography, hydroxyapatite column chromatography, etc.), fractional precipitation, and/or the conventional fractionation methods (for example, collecting target separated materials after electrophoresis, etc.). Filtering and gel chromatography are preferable, but the fractionation methods are not limited to the above.

For example, when the fractionation is performed by filtering, a commercially available filter is suitably selected according to, for example, the molecular weight of one or more irradiation-generated fragments of natural high-molecular weight compound(s). The filtering can be performed in the usual manner or according to the operation instructions included with the filter to be used. Preferable filter units for use in fractionation include ultrafiltration filters such as Ultrafree MC/CL, Centricut, Centriprep, and Microcon (Nihon Millipore K.K.), Attoprep UF (Atto Corporation), Vivaspin (SARTORIUS K.K.), VectaSpin (Whatman), etc., and filters other than the above can also be suitably used.

In the invention, the fraction thus obtained is reacted with one or more antibodies capable of recognizing the one or more irradiation-generated fragments of natural high-molecular weight compound(s).

As "one or more antibodies capable of recognizing the one or more fragments" in this specification, any antibody that reacts with the one or more irradiation-generated fragments of natural high-molecular weight compound(s) can be used, and one or more antibodies capable of undergoing a specific antigen-antibody reaction with the one or more fragments are preferable. More specifically, preferable are one or more antibodies that recognize only one or more fragments whose molecular weight is lowered by irradiation and that do not recognize molecules other than the one or more fragments whose molecular weight is lowered by irradiation, such as one or more fragments generated by factors other than irradiation, non-fragmented natural high-molecular weight compounds, and natural high-molecular weight compounds whose molecular weight is raised by irradiation.

Either a monoclonal antibody or a polyclonal antibody may be used, but a monoclonal antibody is preferable. The antibody can be used alone or in combination. Two or more kinds of antibodies may individually recognize one or more different fragments, and may recognize different antigenic determinants of the same one or more fragments.

The antibody may be generated by the usual method, or a commercially available antibody may be used.

A polyclonal antibody can be produced by the conventional method, and the production of a polyclonal antibody is briefly described. For example, a polyclonal antibody can be produced by immunizing a laboratory animal (e.g., mouse, rat, or rabbit) with an antigen (e.g., one or more fragments of natural high-molecular weight compound(s) obtained from irradiated food) to produce an antibody in the animal, collecting blood from the immunized animal, and purifying the collected blood.

A monoclonal antibody can be prepared by the conventional method, and the production of a monoclonal antibody is briefly described. For example, a monoclonal antibody can be produced by immunizing a laboratory animal with an antigen, removing the spleen from the animal, fusing a removed spleen cell and a myeloma cell, selecting the fused cells with a selection medium (for example, HAT medium), screening a hybridoma producing the target antibody (for example, using ELISA, RIA, etc.), cloning the hybridoma, and purifying an antibody from the hybridoma.

The method for preparing an antibody is disclosed in more detail in the following documents, and the disclosures thereof are incorporated herein by reference "*Zoku Seikagaku Jikken Koza* 5, *Menekiseikagaku Kenkyuho* (*Biochemical Experimental Series-Continued,* 5, *"Immune Biochemistry Study Method"*)", edited by Japanese Biochemical Society (Tokyo Kagaku Dojin), Chapter 1, 1•5 Method for preparing a monoclonal antibody, page 66"; "*Monokuronal kotai sakusei manyuaru* (*Manual for preparing a monoclonal antibody*)", edited by Nobuhiko TADA, Gakusai Kikaku, (October, 1996)"; "*Monokuronal kotai, Seikagaku Jikkenho* (*Monoclonal Antibody, Biochemical Experiment Method*)" edited by Ailsa M. Campbell, translated by Toshiaki OSAWA, Tokyo Kagaku Dojin, (October, 1989); "*Tankuron kotai-Chosei to kyarakutarizeshon* (*Monoclonal antibody-Preparation and characterization*) *Hirokawa kagaku to Seibutsujikken rain* (8) (*Hirokawa Chemistry and Bioexperiment line* (8)", edited by Hideaki NAGAMUNE, Hiroshi TERADA, Hirokawa Shoten, (1990); "*Tankuronkotai jikken sosa nyumon* (*Monoclonal Antibody; Introduction of Experimental Procedure,* edited by Tamie ANDO and Takeshi CHIBA, Kodansha, (1991)"; "Birch, J. R., ed. (1995) *Monoclonal Antibodies: Principles and Applications Wiley-Liss.*"; "Goding, J. W. (1996) *Monoclonal Antibodies: Principles and Practice. Production and Application of Monoclonal Antibodies in Cell Biology, Biochemistry, and Immunology,* $3^{rd}$ ed. Academic Press.*"; "*Harlow, E., and D. Lane. (1988) *Antibodies: A Laboratory Manual,* Cold Spring Harbor Laboratory, Chapter 6, Monoclonal Antibodies, and Chapter 7, Growing Hybridomas."; "G. Kohler and C. Milstein. (1975) *Continuous cultures of fused cells secreting antibody of predefined specificity, Nature* 256: 495-497."; "de St Groth S F, Scheidegger D. *Production of monoclonal antibodies: strategy and tactics. J. Immunol Methods,* (1980); 35(1-2): 1-21.", etc. Antibodies produced according to methods disclosed in other references on antibodies can also be used in the invention.

Preferable antigens for use in the preparation of an antibody include one or more fragments whose detection sensitivity can be improved, and, for example, one or more irradiation-generated fragments of natural high-molecular weight compound(s), the content of which is high in food, one or more irradiation-generated fragments of natural high-molecular weight compound(s) whose molecular weight is easily lowered by irradiation, or one or more irradiation-generated fragments of natural high-molecular weight compound(s) which cannot be easily decomposed by heat-treatment. For example, when an egg is used as a food, one or more irradiation-generated fragments of ovalbumin, the content of which is high in an egg, can be used. In the case of beef used as a food, one or more irradiation-generated fragments of bovine serum albumin can be used. In addition to these fragments, the following fragments may possibly be used for the preparation of an antibody: one or more irradiation-generated fragments of pig serum albumin in the case of pork as a food; one or more irradiation-generated fragments of Pen a 1 in the case of shrimp as a food; one or more irradiation-generated fragments of glutenin, gliadin, or other seed storage protein (globulin and albumin) in the case of wheat as a food; one or more irradiation-generated fragments of glutenin or gliadin in the case of a wheat processed food as a food; one or more irradiation-generated fragments of Gly m 1 in the case of soybean as a food; and one or more irradiation-generated fragments of seed storage protein in the case of pepper as a food.

When the one or more irradiation-generated fragments are one or more kinds of protein, a protein which is expressed in a host by conventional gene manipulation can also be used as an antigen for use in the preparation of an antibody. For example, according to the conventional gene manipulation, the amino acid sequence or sequences of one or more fragments generated by irradiation is/are determined using N-terminal analysis, C-terminal analysis, mass analysis, etc.; a nucleic acid coding the amino acid sequence is obtained by PCR in which a genome extracted from a food is used as a template, chemical synthesis, gene cloning, etc.; the nucleic acids are incorporated into an expression vector; and the resultant is introduced to a suitable host (for example, coli bacillus, yeast, an animal cell, etc.), thereby expressing the target protein. The protein thus expressed can be used as an antigen for preparing an antibody.

Examples of a commercially available antibody include an anti-bovine serum albumin antibody (AbCam Limited, AB3781 mouse anti-BSA monoclonal antibody (clone: BSA-7G10)), (Biogenesis Ltd., 0220-1239 (clone: BGN/B-2), 0220-1259 (clone: BGN/D1), 0220-1279 (clone: BGN/H8), (Sigma, B2901 (clone: BSA-33)), an anti-pig serum albumin antibody (Bethyl Laboratories, Inc., A100-210A goat anti-Pig albumin antibody), anti-chicken ovalbumin antibody (Sigma, A6075 (clone: OVA-14)"), etc.

In the invention, the antibody thus produced is reacted with a fraction containing the above-mentioned one or more irradiation-generated fragments of natural high-molecular weight compound(s) to detect the above-mentioned one or more fragments.

Examples as a method for detecting one or more fragments include conventional methods utilizing the specificity of the antigen-antibody reaction, such as enzyme immunoassays (EIA) (e.g., ELISA (enzyme-linked immunosorbent assay)), fluorescent immunoassay (FIA), RI immunoassay (RIA), immunochromatography, Dot Blotting, surface plasmon resonance, antibody array (Suspension Bead Array), and the like, or conventional methods which optically detect an agglutination reaction or a precipitation reaction, such as turbidimetric immunoassay (TIA), immunoprecipitation methods, and the like, and other detection methods other than the above-mentioned methods are also applicable. Among the above, ELISA and immunochromatography are preferable.

Alternatively, commercially available detection kits may be used, and FASTKIT immunochromato egg (Japan BD) can be mentioned as an example, but such kits are not limited thereto. In particular, an immunochromatography enables the simple detection of irradiation treatment of foods.

If required, a sample of irradiated food is compared with a sample of non-irradiated food or a sample of food irradiated at a predetermined dose. This comparison allows determination as to whether or not food to be detected by the invention has been irradiated.

The invention also relates to a kit for detecting irradiation treatment of foods as follows.

The kit of the invention is equipped with a fractionator for obtaining from a food sample a fraction containing one or more irradiation-generated fragments of natural high-molecular weight compound(s) and one or more antibodies capable of recognizing the one or more fragments.

Any apparatus can be used as the "fractionator" of the kit of the invention insofar as the apparatus (including a machine or device) can fractionate the above-mentioned food sample. Examples of such apparatuses include filter devices (e.g., the above-mentioned filter membrane and a filter device equipped with a sample reservoir, a sample vial, and/or a syringe), column chromatography equipment (e.g., a microspin column for gel chromatography and column chromatography equipment provided with a sample reservoir, a sample vial, and/or a syringe), a solid phase extraction device (e.g., a solid phase extraction cartridge and a solid phase extraction device provided with a sample reservoir, a sample vial, and/or a syringe), a separation precipitation device (e.g., fractional precipitation device equipped with a solvent suitable for fractionating fragments, a mini centrifugation tube, and a sample vial), etc., and other fractionators other than these are applicable.

A container or a housing, such as a sample reservoir, sample vial, or a syringe, is preferably made of a material which does not easily adsorb the target (i.e., one or more irradiation-generated fragments of natural high-molecular weight compound(s)) and has a high reagent resistance. For example, a material coated with a suitable blocking agent, a fluoride-based resin, polypropylene, polyethylene, or the like is desirable.

The "one or more antibodies capable of recognizing the one or more fragments" provided for the kit of the invention is as described above. There is no limitation to the manner of housing the one or more antibodies in a kit insofar as the function of the one or more antibodies is not deteriorated. For example, the one or more antibodies can be placed in a suitable container as it is or suspended in a solvent, and is further housed in a package (box, bag, etc.) for a kit. The one or more antibodies are preferably kept in a frozen or refrigerated state.

The kit of the invention may be further equipped with a pre-filtering device. As the pre-filtering device, the above-mentioned prefilter membrane, and the above-mentioned device equipped with a sample reservoir, a sample vial, and/or a syringe, or the like is mentioned, and other units rather than these units can also be used.

The kit of the invention may be equipped with various reagents for detecting irradiation treatment of foods. Examples of such reagents are as follows: reagents for preparing a food sample (e.g., a solution or solvent in which food is suspended, or a cleaning liquid, and/or concentrations thereof), reagents for use in heat-treatment (e.g., SH oxidizing agents/reducing agents, surfactants, pH control agents, and/or concentrations thereof), reagents for detecting one or more fragments (e.g., secondary antibodies, enzyme labeled secondary antibodies, fluorescent labeled secondary antibodies, magnetic labeled secondary antibodies, biotin labeled secondary antibodies, enzyme labeled avidins, fluorescent labeled avidins, magnetic labeled avidins, colorimetric substrates for ELISA), plate cleaners, food samples for control (e.g., samples of food irradiated at a given dose and/or non-irradiated food), etc.

BEST MODE FOR CARRYING OUT THE INVENTION

Figure 1:
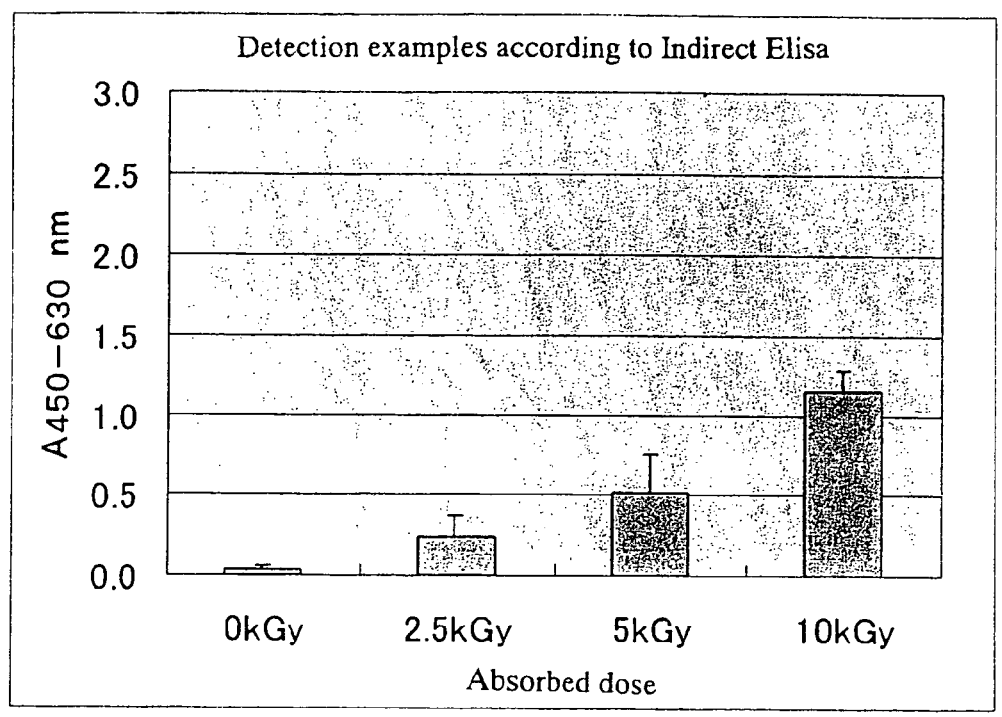
FIG. 1 shows an example of detecting an irradiated egg by a novel detection method (Indirect ELISA). In a sample obtained from γ-ray irradiated eggs, the reaction in Indirect ELISA was intensified in proportion to the absorbed dose. In contrast, in a non-irradiated control sample (0 kGy), the reaction in Indirect ELISA is hardly seen. This shows that it can be detected whether an egg in its shell has been subjected to an irradiation treatment. Note that the data shown here graphically represent the average of three independent indirect ELISAs.

Hereinafter, the present invention is described in detail with reference to Examples, but is not limited thereto.

EXAMPLE 1

Preparation of Irradiated Eggs

Eggs to be irradiated were purchased at a food counter of the Takasaki Station Building. (The eggs were purchased on Jul. 15, 2002 (Heisei 14), Fresh Egg, size L, domestic product, expiration-date: Jul. 21, 2002, packed by: Gumma Chicken Egg GP Center). The eggs in their shells were subjected to γ-ray irradiation at the Japan Atomic Energy Research Institute (now referred to as the Japan Atomic Energy Agency), the 6th irradiation room of the Cobalt Irradiation Facility No. 2 of the Takasaki Research Institute (now referred to as the Takasaki Advanced Radiation Research Institute). Absorbed doses were set to 2.5, 5.0, and 10.0 kGy, and each absorbed dose per hour was calculated in view of the distance from the radiation source. Irradiated whole eggs were transferred to an experimental facility at 4° C., and then kept at −80° C. as they were.

EXAMPLE 2

Preparation of Whole Egg Dilutions

Each irradiated whole egg was defrosted at room temperature, and each egg liquid was placed in a beaker, followed by stirring with a homogenizer. The result was diluted with 50 mM Tris-HCl buffer with a pH of 7.6 (Sigma) to adjust the protein concentration to 1.5 mg/mL. The protein concentration was measured using a protein assay kit II (Bio-Rad, Standard Method), and was determined using bovine serum albumin (BSA) as standard. Each whole egg dilution thus obtained was dispensed into cryopreservation tubes, and kept at −20° C.

EXAMPLE 3

Heating, Cooling, and Filtering Irradiated Whole Egg Dilutions

Reduced glutathione (GSH) and oxidized glutathione (GSSG) were separately dissolved in ultrapure water to 500 mM. Each solution was dispensed into cryopreservation tubes, freeze-preserved at −20° C., and then defrosted for use.

Each sample of whole egg freeze-preserved dilution was defrosted at room temperature, and then dispensed into screw cap tubes (SCT-200-SS-C, Axygen) in 400 μL amounts. Subsequently, 1 μL of reduced glutathione solution was added, and the result was stirred with a vortex. 3 μL of oxidized glutathione solution was then added, and further stirred with a vortex (GSH:GSSG=1:3). The result was heated in boiling water for 10 minutes, and then cooled in running water for 1 hour. The cooled sample was stirred with a vortex, and centrifuged using a microcentrifuge (about 14000 g, at 4° C. for 20 minutes) to remove insoluble proteins. The entire quantity of the supernatant thus obtained of each sample was collected with a 1-mL tuberculin syringe, and filtered by a 0.45-μm hydrophilic PVDF membrane prefilter (Millex, Millipore). The filtrate was collected on a spin filter for direct ultrafiltration (ultrafree MC, biomax-PB-polyethersulfone membrane, fraction molecular weight of 30000, Millipore), and subsequently ultrafiltrated with a microcentrifuge (about 5000 g, at 4° C. for 40 minutes).

EXAMPLE 4

Indirect ELISA Using an Anti Ovalbumin Antibody

Each sample obtained by the above heating, cooling, and filtering was dispensed in 50-μL amounts into an ELISA microplate (96 wells, flat bottom, high binding, polystyrene, Greiner), and dried at 37° C. overnight to be coated. 0.2% milk casein/5% fetal bovine serum/TBS* was used for blocking (room temperature, 2-hour incubation). The ELISA plate was washed 3 times in every step using 0.1% Tween20/TBS*. Mouse anti ovalbumin monoclonal antibodies (clone OVA-14, Sigma) were used as a primary antibody, and diluted 10000 times with 5% fatal bovine serum/TBS*. The dilution was added at 100 μL/well, and the mixture was incubated for 90 minutes at room temperature. Goat anti mouse IgG HRP-conjugates (Upstate Biotechnology, Inc.) were used as a secondary antibody, and was diluted 5000 times with 5% fetal bovine serum/TBS*. The dilution was added at 100 μL/well, and the mixture was incubated at room temperature for 90 minutes. A TMB Peroxidase EIA Substrate Kit (Bio-Rad) was used as a colorimetric reagent, and added to each mixture at 100 μL/well. Subsequently, 100 μL of 1N sulfuric acid solution was then added to stop the reaction. The ELISA reaction was evaluated by reading the difference in the absorbances at 450 nm and 630 nm with a microplate reader (trade name "Model 3550", Bio-Rad). The results are shown in FIG. 1.

TBS*: Tris Buffered Saline (200 mM Tris-HCl/1.5 M NaCl, pH 7.6)

In the samples obtained from the γ-ray irradiated whole egg, the reaction in Indirect ELISA was intensified in relation to the absorbed dose. In contrast, in the non-irradiated control sample (0 kGy), the reaction in Indirect ELISA was hardly observed. This shows that it is possible to detect whether or not an egg in its shell has been irradiated (FIG. 1).

EXAMPLE 5

Detection Using a Commercially-Available Immunochromatography Kit

Figure 2:
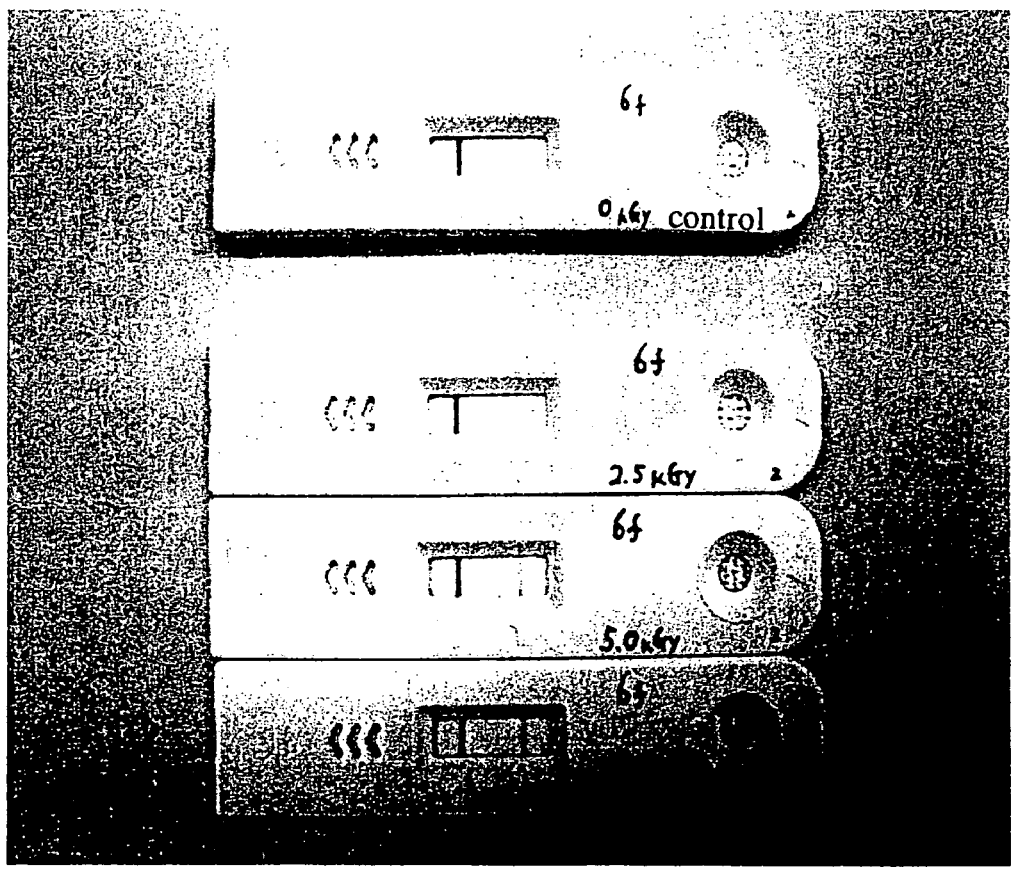
FIG. 2 is a detection example using a commercially-available immunochromatography kit. In irradiated samples (absorbed dose: 2.5 kGy, 5.0 kGy, 10.0 kGy), a purplish red line was observed at the judgment part (T) while in a sample obtained from a non-irradiated control egg, no purplish red line was observed at the judgment part (T).

ELISA is a commonly used technique; however, an immunochromatography method is known as a further simple and low-cost method. This Example shows a case where the immunochromatography method was applied to each egg sample obtained by following the procedures in Examples 1 to 3. A FASTKIT IMMUNOCHROMATO EGG (Japan BD) was used for the immunochromatography. Each sample obtained by following the procedures in Examples 1 to 3 was first diluted 6 times with a dilution buffer that comes with the FASTKIT IMMUNOCHROMATO EGG, and 100 μL thereof was added by drops using a micro pipette to a sample drop well of a test plate. According to the operation manual included with the kit, the test plate was allowed to stand on a level stand, and after 15 minutes, visually observed. The results are shown in FIG. 2.

In a non-irradiated egg control sample, no purplish red line was observed at the judgment part (T) while in irradiated samples (absorbed dose: 2.5 kGy, 5.0 kGy and 10.0 kGy), a purplish red line was observed at the judgment part (T). This shows that the combination of the procedures of Examples 1 to 3 of the invention and the commercially available immunochromatography kit provides a very simple and novel detection method which makes it possible to determine the non-irradiated control as negative and the samples irradiated at doses of 2.5 kGy, 5.0 kGy, and 10.0 kGy as positive (FIG. 2).

EXAMPLE 6

Detection of Irradiated Egg White Powder (Trade Name "SANKIRARA")

Egg white powder (trade name "SANKIRARA ADL", TAIYO KAGAKU CO., LTD., Shiohama Factory, Lot No. 104171) was put in plastic bags, irradiated by the procedure of Example 1, and kept at −20° C. Subsequently, each bagged egg white powder portion kept at −20° C. was dissolved (suspended) with the buffer and the protein concentration measurement method of Example 2 in such a manner that the protein concentration was 24 mg/mL. The dilution of each egg white powder portion thus obtained was serially diluted to prepare dilutions of white egg powder with protein concentrations of 6.0 mg/mL or 1.5 mg/mL. The obtained samples were treated in the same manner as in Examples 3 and 4, and Indirect ELISA was carried out. The results are shown in FIG. 3.

Figure 3:
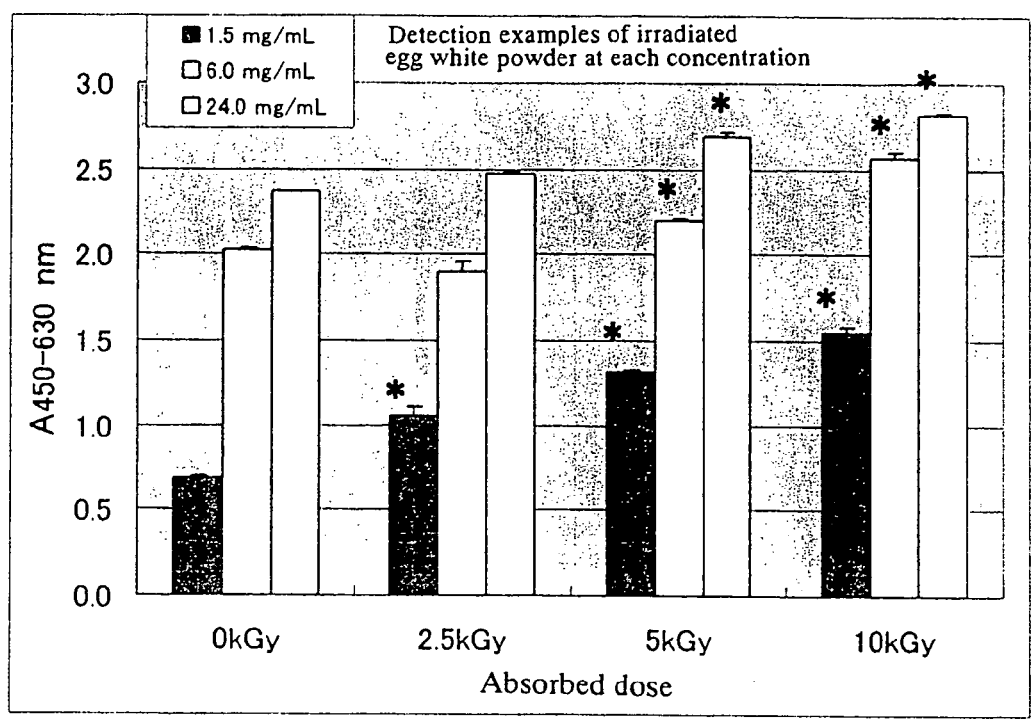
FIG. 3 shows a detection result obtained by a novel detection method (Indirect ELISA) of irradiated egg white powder (trade name "SANKIRARA"). The mark "*" in FIG. 3 indicates that the irradiated egg white powder shows statistical significance of difference with P<0.05 as compared with the non-irradiated control. Also in egg white powder that was quite well processed, a significant difference from the non-irradiated control was observed at a suitable concentration (1.5 mg/mL in Examples of the invention).

Using the invention, even with well processed egg white powder, a significant difference from the non-irradiated control was observed at a suitable concentration (1.5 mg/mL in this example) (FIG. 3).

EXAMPLE 7

Preparation of an Irradiated Bovine-Serum-Albumin Solution

It was confirmed that a test substance other than an egg was able to be detected as described below.

A given amount of bovine serum albumin (A-7030, Sigma) was weighed out and then diluted with 50 mM Tris-HCl buffer with a pH of 7.6 (Sigma) to 24 mg/mL. This dilution was used as the bovine serum albumin sample to be irradiated. The γ-ray irradiation of a bovine serum albumin solution was entrusted to the Japan Radioisotope Association Koga Laboratory. The bovine serum albumin solution was transported under dry ice cooling, and irradiated in a frozen state. The irradiated bovine serum albumin solution returned from Japan Radioisotope Association was defrosted at room temperature, and immediately the solution was dispersed in cryopreservation tubes, and then kept at −80° C. The experimentally measured dose of the irradiated bovine serum albumin solution was 9.8 kGy-10.8 kGy when the absorbed dose was set to 10.0 kGy.

EXAMPLE 8

Heating, Cooling, and Filtering an Irradiated Bovine Serum Albumin Solution

The above freeze-preserved solution of bovine serum albumin was defrosted at room temperature, the concentration was adjusted with Tris-HCl buffer, and then the result was dispensed into screw cap tubes (SCT-200-SS-C, Axygen) in 400-μL amounts. Subsequently, 10 μL of 2-mercaptoethanol (Wako Pure Chemical Industries, Ltd.) was added, and the results were stirred with a vortex, thereby adjusting the final concentration of 2-mercaptoethanol to 2.5%. Each result was heated in boiling water for 7.5 minutes, and then cooled in running water for 1 hour. Each cooled sample was stirred with a vortex, and centrifuged using a microcentrifuge (about 14000 g, at 4° C. for 20 minutes) to remove insoluble proteins. The entire quantity of supernatant thus obtained of each sample was collected with a 1-mL tuberculin syringe, and filtrated by a hydrophilic PVDF membrane prefilter with a pore size of 0.45 μm (trade name "Millex HV", Millipore). The filtrate was directly collected on a spin filter for ultrafiltration (ultrafree MC, biomax-PB-polyethersulfone membrane, with a fraction molecular weight of 10000, Millipore) that was blocked with 5% rabbit serum (Cosmo Bio. Co., Ltd.)/TBS), and subsequently ultrafiltrated with a microcentrifuge (about 5000 g, at 4° C. for 20 minutes)

EXAMPLE 9

Indirect ELISA Using an Anti Bovine Albumin Antibody

Figure 4:
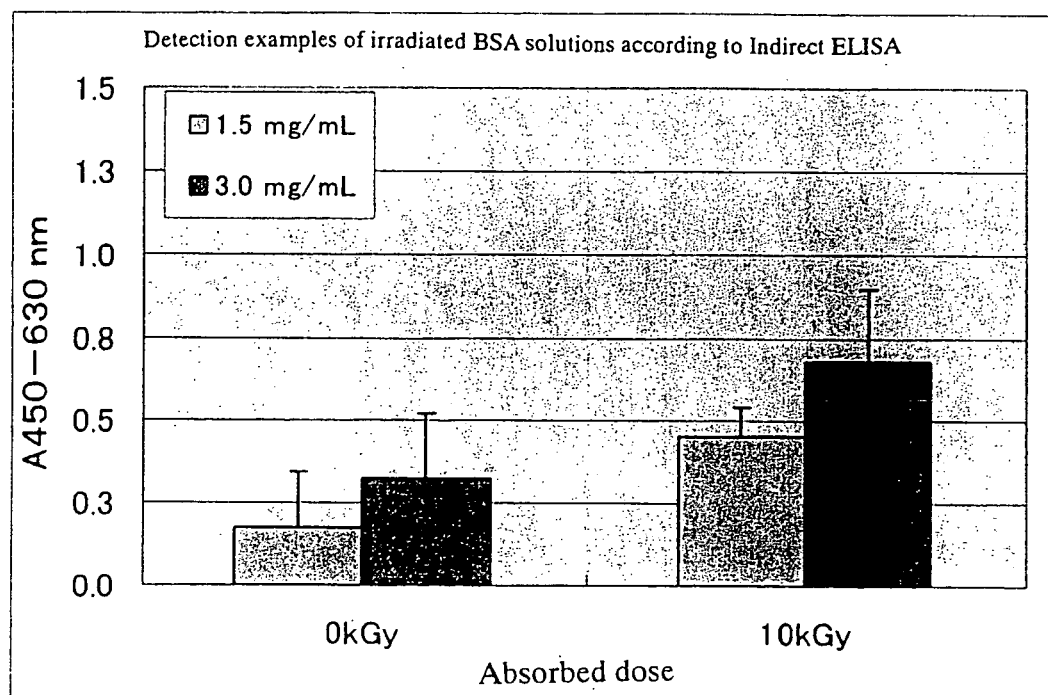
FIG. 4 shows a detection result obtained by a novel detection method (Indirect ELISA) of an irradiated bovine serum albumin solution. In a sample (10.0 kGy) obtained from a γ-ray irradiated bovine serum albumin solution, the reaction in Indirect ELISA was significantly intensified as compared with that of the non-irradiated control sample (0 kGy) (a probability level of 5%). This shows that it is possible to detect whether or not the bovine serum albumin solution has been irradiated. Note that the data shown here graphically represent the average of five indirect ELISAs.

Each sample obtained by the above heating, cooling, and filtering was dispensed in 50-μL amounts into an ELISA microplate (96 wells, flat bottom, high binding, polystyrene, Greiner), and dried at 37° C. overnight for coating. 5% rabbit serum/TBS was used for blocking (room temperature, 2-hour incubation). The ELISA plate was washed 3 times in every step using 0.1% Tween 20/TBS. Mouse anti-bovine serum albumin monoclonal antibodies (clone BSA-33, Sigma) were used as a primary antibody, and diluted 10000 times with 5% rabbit serum/TBS. The dilution was added at 100 μL/well, and each mixture was incubated for 90 minutes at room temperature. Rabbit anti mouse IgG HRP-conjugates (Dako-Cytomation) were used as a secondary antibody, and diluted 2000 times with 5% rabbit serum/TBS. The dilution was added at 100 μL/well, and the mixture was incubated at room temperature for 90 minutes. A TMB Peroxidase EIA Substrate Kit (Bio-Rad) was used as a colorimetric reagent, and added to each mixture at 100 μL/well. Subsequently, 100 μL of 1N sulfuric acid solution was then added to stop the reaction. The ELISA reaction was evaluated by reading the difference in the absorbances at 450 nm and 630 nm using a microplate reader (trade name "Model 3550", Bio-Rad). The results are shown in FIG. 4. Samples obtained from the γ-ray irradiated bovine serum albumin solution (10 kGy) show a significantly intensified reaction in Indirect ELISA as compared with a non-irradiated control sample (0 kGy). This shows that it is possible to detect whether or not a bovine serum albumin solution has been treated by irradiation (FIG. 4).

EXAMPLE 10

In the case of the detection of irradiated beef, the detection method of the invention may be carried out as follows.

Beef (2 g) and a solvent (50 mM Tris-HCl buffer, +2.5% 2-ME, pH 7.6, 38 mL) are ground in a food processor. The result is centrifuged (14000 g, at 4° C. for 20 minutes), and the supernatant is collected. The concentration of the collected supernatant is adjusted with Tris-HCl buffer, and the result is dispersed in 400-μL amounts into screw cap tubes (SCT-200-SS-C, Axygen). Subsequently, heating, cooling, prefiltering, and filtering are conducted in the same manner as in Example 8. Each sample obtained is subjected to Indirect ELISA in the same manner as in Example 9. In this Indirect ELISA, anti bovine serum albumin antibodies (AbCam Limited, AB3781 mouse anti-BSA monoclonal antibody (clone: BSA-7G10);

0220-1239 (clone: BGN/B2), 0220-1259 (clone: BGN/D1), and 0220-1279 (clone: BGN/H8) of Biogenesis Ltd.; and B2901 (clone: BSA-33) Sigma may be used. By comparing the irradiated sample and the non-irradiated control and examining the comparison results, it is possible to detect whether or not beef has been treated by irradiation.

EXAMPLE 11

In the case of the detection of irradiated pork, the detection method of the invention may be carried out as follows.

Pork (2 g) and a solvent (50 mM Tris-HCl buffer, +2.5% 2-ME, pH 7.6, 38 mL) are ground in a food processor. The result is centrifuged (14000 g, at 4° C. for 20 minutes), and the supernatant is collected. The concentration of the collected supernatant is adjusted with Tris-HCl buffer, and the reult is dispersed in 400-μL amounts into screw cap tubes (SCT-200-SS-C, Axygen). Subsequently, heating, cooling, prefiltering, and filtering are conducted in the same manner as in Example 8. Each sample obtained is subjected to Indirect ELISA in the same manner as in Example 9. In this Indirect ELISA, anti-pig serum albumin antibodies (Bethyl Laboratories, Inc., A100-210A goat anti-Pig albumin antibody) may be used. By comparing the irradiated sample and the non-irradiated control and examining the comparison results, it is possible to detect whether or not pork has been treated by irradiation.

EXAMPLE 12

In the case of detecting irradiated shrimp, the detection method of the invention may be carried out as follows.

Shrimp tail meat (2 g) and a solvent (50 mM Tris-HCl buffer, +5 mM glutathione (GSH:GSSG=1:3), pH 7.6, 38 mL) are ground in a food processor. The result is centrifuged (14000 g, at 4° C. for 20 minutes), and the supernatant is collected. The concentration of the collected supernatant is adjusted with Tris-HCl buffer, and the result is dispersed in 400-μL amounts into screw cap tubes (SCT-200-SS-C, Axygen). Subsequently, heating, cooling, prefiltering, and filtering proceses are conducted in the same manner as in Example 3. Each sample obtained is subjected to Indirect ELISA in the same manner as in Example 4. In this indirect ELISA, monoclonal antibodies against shrimp allergy (Jeoung B J., et al., J. Allergy Clin. Immunol., (1997), 100: 229-234) may be used. By comparing the irradiated sample and the non-irradiated control and examining the comparison results, it is possible to detect whether or not shrimp has been treated by irradiation.

EXAMPLE 13

In the case of detecting an irradiated soybean, the detection method of the invention may be carried out as follows.

Soybean (2 g) and a solvent (50 mM Tris-HCl buffer, +5 mM glutathione (GSH:GSSG=1:3), pH7.6, 38 mL) are ground in a food processor. The soybean milk-like result is centrifuged (14000 g, at 4° C. for 20 minutes), and the supernatant is collected. The concentration of the collected supernatant is adjusted with Tris-HCl buffer, and the result is dispersed in 400-μL amounts into screw cap tubes (trade name "SCT-200-SS-C", Axygen). Subsequently, heating, cooling, prefiltering, and filtering processes are conducted in the same manner as in Example 3. Each sample obtained is subjected to Indirect ELISA in the same manner as in Example 4. In this indirect ELISA, monoclonal antibodies against soybean allergy ((Samoto M., et al., Biosci. Biotechnol. Biochem., (1994), 58: 2123-2125) (Gonzalez R., et al., Allergy., (2000), 55: 59-64) maybe used. By comparing the irradiated sample and the non-irradiated control and examining the comparison results, it is possible to detect whether or not soybeans have been treated by irradiation.

It will be understood that the invention makes it possible to detect various irradiation of foods in addition to those of the Examples above (e.g., vegetables, fruits, and spices). Thus, in the case of the irradiation treatment of foods other than those of the Examples above, usable antibodies include antibodies produced by the above-described methods herein, antibodies produced by methods described in other references on antibody production, or commercially-available antibodies. For example, the following antibodies may be used in the invention: an anti-fish meat monoclonal antibody (Asensio L., et al., *J. Food Prot.*, (2003), 66: 886-889), a monoclonal antibody against cooked meat (Hsieh Y H., et al., *J. Food Prot.*, (1998), 61: 476-481), a monoclonal antibody against garlic (Wen G Y., et al., *J. Cell Biochem.*, (1995), 58:481-489), a monoclonal antibody against wheat gliadin (Ellis H J, Freedman A R, Ciclitira P J. The production and characterisation of monoclonal antibodies to wheat gliadin peptides. *J. Immunol Methods* (Jun. 2, 1989,); 120(1): 17-22, and Ellis H J and Doyle A P, Wieser H, Sturgess R P, Day P, Ciclitira P J. Measurement of gluten using a monoclonal antibody to a sequenced peptide of alpha-gliadin from the coeliac-activating domain I. *J. Biochem Biophys Methods* (January, 1994); 28 (1): 77-82), and the like.

INDUSTRIAL APPLICABILITY

The invention provides a novel method which enables to detect irradiation treatment of foods simply, rapidly, and reliably. Since the method of the invention detects one or more fragments generated by irradiation, the method has an advantage that the detection result is not sensitive to the state of a food sample, unlike the pulsed photostimulated luminescence (PSL) method in which the sensitivity decreases due to light or heat, or the electron spin resonance (ESR) method in which the spectrum weakens over time.

The method of the invention detects one or more fragments generated by irradiation. Thus, the method of the invention has an advantage that it is applicable to food samples sterilized by means other than irradiation (e.g., heat sterilization), unlike the method of determining the viable cell count, which is one of the conventional methods.

Moreover, the method of the invention also has an advantage in that it requires neither expensive measurement equipment nor highly-skilled engineers.

Since the invention provides a simple, rapid, and reliable method, it will likely find wide use in many countries, including Japan, Europe, and the U.S, to replace the currently used methods of detecting irradiation of foods.

The method and kit of the invention allow even dealers and companies which do not specialize in the inspection of irradiation of foods (e.g., food brokers, food handling contractors, food processing companies, etc.) to easily detect irradiation of foods when importing or otherwise receiving food or when exporting or shipping food.

If the method of the invention were authorized as a domestic or international standard analytical method for irradiation of foods, it would offer a new quality assurance system for securing the safety and reliability of food to consumers at low cost.

What is claimed is:

1. A method for detecting irradiation treatment of food comprising the steps of:
   (A) obtaining a fraction containing one or more irradiation-generated fragments of a natural high-molecular weight compound from an irradiated food sample by fractionating an irradiated food sample and removing a fraction containing a non-fragmented natural high-molecular weight compound and its aggregates raised by irradiation, and (B) reacting the obtained fraction with one or more antibodies that are capable of recognizing the one or more irradiation-generated fragments, thereby detecting the one or more irradiation-generated fragments.

2. A method according to claim 1, wherein the fractionation is performed by ultrafiltration.

3. A method according to claim 1, further comprising, prior to the step (A), a step of pre-filtrating the food sample.

4. A method according to claim 1, wherein in the step (B), the one or more fragments are detected by at least one method selected from the group consisting of ELISA (enzyme-linked immunosorbent assay) and immunochromatography.

5. A method according to claim 1, wherein the food is at least one member selected from the group consisting of eggs, meat, fish and shellfish, spices, herbs, cereals, potatoes, vegetables, seeds, mushrooms, fruit, seaweed, milk, and processed foods thereof.

6. A method according to claim 5, wherein the food is at least one member selected from the group consisting of chicken eggs, beef, pork, shrimp, wheat, soybeans, black pepper, white pepper, sesame, nutmeg, cabbage, welsh onion, and processed foods thereof.

7. A method according to claim 1, wherein the natural high-molecular weight compound is a protein.

8. A method according to claim 1, wherein a molecular weight of the one or more fragments is 30000 or less.

9. A method according to claim 1, wherein the one or more antibodies are monoclonal antibodies.

10. A method according to claim 1, wherein the one or more antibodies are polyclonal antibodies.

11. A method according to claim 1, wherein the obtained fraction does not contain the non-fragmented natural high-molecular weight compound(s).

* * * * *